US009260685B2

(12) United States Patent
Herzog

(10) Patent No.: US 9,260,685 B2
(45) Date of Patent: Feb. 16, 2016

(54) SYSTEM AND PLANT FOR CULTIVATION OF AQUATIC ORGANISMS

(75) Inventor: Ra'anan Herzog, Tel-Aviv (IL)

(73) Assignee: UNIVERVE LTD., Tel Aviv (IL)

( * ) Notice: Subject to any disclaimer, the term of this patent is extended or adjusted under 35 U.S.C. 154(b) by 0 days.

(21) Appl. No.: 13/578,857

(22) PCT Filed: Feb. 15, 2011

(86) PCT No.: PCT/IL2011/000159
§ 371 (c)(1),
(2), (4) Date: Aug. 14, 2012

(87) PCT Pub. No.: WO2011/099016
PCT Pub. Date: Aug. 18, 2011

(65) Prior Publication Data
US 2012/0309081 A1    Dec. 6, 2012

Related U.S. Application Data

(60) Provisional application No. 61/304,525, filed on Feb. 15, 2010.

(51) Int. Cl.
*C12M 1/34* (2006.01)
*C12M 1/00* (2006.01)

(52) U.S. Cl.
CPC .............. *C12M 23/18* (2013.01); *C12M 21/02* (2013.01); *C12M 23/02* (2013.01); *C12M 23/26* (2013.01); *C12M 29/06* (2013.01); *C12M 31/04* (2013.01); *C12M 31/10* (2013.01)

(58) Field of Classification Search
CPC ...... C12M 21/02; C12M 23/02; C12M 23/18; C12M 23/26; C12M 29/06; C12M 31/04; C12M 31/10
USPC ................................. 435/288.7, 289.1, 292.1
See application file for complete search history.

(56) References Cited

U.S. PATENT DOCUMENTS 5,158,037 A    10/1992  Engelbart
2008/0160591 A1  7/2008  Willson et al.
(Continued)

FOREIGN PATENT DOCUMENTS

BE    1011897 A6    2/2000
WO    96/21723 A1   7/1996
(Continued)

OTHER PUBLICATIONS

The International Search Report for International Application No. PCT/IL2011/000159, two pages, mailed Jun. 9, 2011.

*Primary Examiner* — Nathan Bowers
*Assistant Examiner* — Timothy Barlow
(74) *Attorney, Agent, or Firm* — Vorys, Sater, Seymour & Pease LLP

(57) ABSTRACT

Provided are a cultivating system for cultivating aquatic organisms including a load-bearing structure having a top portion with at least two top rims transverse to each other and defining a top portion, a bottom portion, and flexible tank adapted for receiving therein a growing medium and for cultivating therein aquatic organisms. Further, the tank can include at least two sidewalls extending such that at least in one cross-section taken along a plane perpendicular to said top portion, at least two of the sidewalls form a general V-shape converging towards the bottom portion. The system can also include a gas emitting arrangement linkable to a source of pressurized gas and comprising gas emitting nozzles disposed within the flexible tank at the bottom portion.

27 Claims, 14 Drawing Sheets

(56) References Cited

U.S. PATENT DOCUMENTS

| | | |
|---|---|---|
| 2008/0311646 A1 | 12/2008 | Cong et al. |
| 2008/0311649 A1 | 12/2008 | Cloud et al. |
| 2009/0130706 A1* | 5/2009 | Berzin et al. ............... 435/292.1 |
| 2009/0215155 A1 | 8/2009 | Cloud et al. |
| 2010/0055764 A1* | 3/2010 | Martin .................. C12M 23/14 435/297.1 |

FOREIGN PATENT DOCUMENTS

| | | |
|---|---|---|
| WO | 2004/008845 A1 | 1/2004 |
| WO | 2004/074423 A2 | 9/2004 |
| WO | 2005/079560 A1 | 9/2005 |
| WO | WO 2008/076998 * | 6/2008 |
| WO | 2009/153790 A1 | 12/2009 |

* cited by examiner

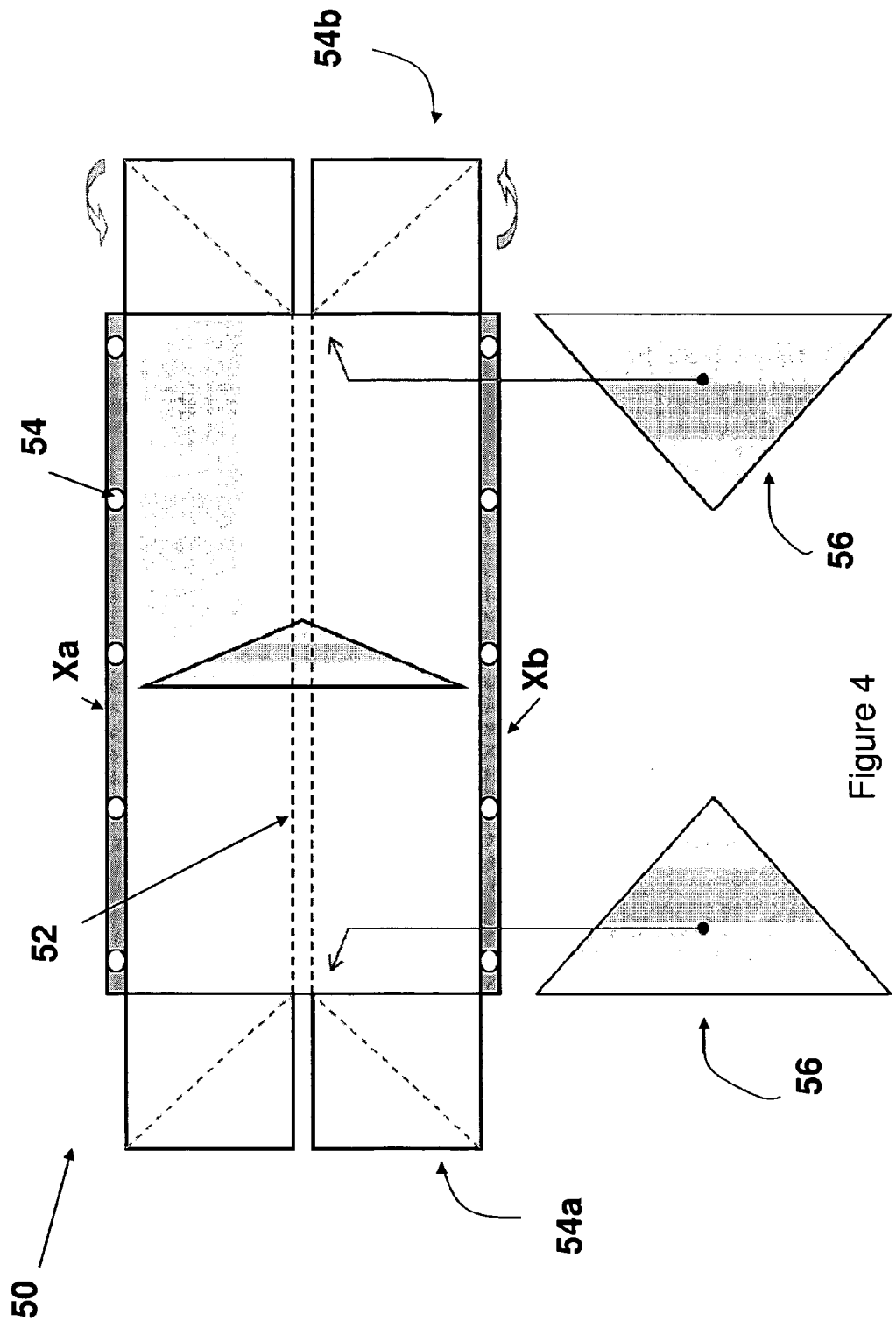

SYSTEM AND PLANT FOR CULTIVATION OF AQUATIC ORGANISMS

This is a National Phase Application filed under 35 U.S.C. §371 as a national stage of PCT/IL2011/000159, filed on Feb. 15, 2011, an application claiming the benefit under 35 U.S.C. §119(e) of U.S. Provisional Application No. 61/304,525, filed on Feb. 15, 2010, the content of each of which is hereby incorporated by reference in their entirety.

FIELD OF THE INVENTION

This invention relates to systems for cultivating aquatic organisms, in particular, micro-algae.

BACKGROUND OF THE INVENTION

Cells of micro-algae (in short "algae") are rich in various bioactivity substances such as proteins, amino acids, carbohydrates, vitamins, antibiotics, highly unsaturated fatty acids, polysaccharides, and colorants. This makes algae great resources with high economic value. Some algae possess abilities to produce hydrocarbons and oil lipids, and thus have promising application in field of renewable energy production. For example, algae lipids can be processed into biodiesel and/or jet-fuel (third generation feedstock for Biofuel), sugar and hydrocarbons into ethanol, and potentially into hydrogen, methanol and bio-power, while the residual biomass (such as proteins, pigments, etc.) can be used for pharmaceuticals, neutraceuticals, cosmetics, fishmeal, biochar, or other applications.

Algae can double in volume overnight and can be continuously harvested on a daily basis. Algae need sunlight, carbon-dioxide, water, nutrients and temperature for their growth. The algal cells fix carbon-dioxide through photosynthesis and carbon usually comprises more than half of its dry weight. Therefore, sufficient carbon source and sunlight are needed during algae cultivation.

There are two main types of large scale algae biomass production systems: open and closed (photobioreactors).

Open systems can be categorized into natural waters (lakes, lagoons, ponds) and artificial ponds or containers. The most commonly used systems include shallow big ponds, tanks, circular ponds, raceway ponds and high-rate ponds (HRP). One advantage of open ponds is that they are easier and cheaper to construct and operate than most closed systems. However, a limitation in open ponds includes poor light utilization by the cells, evaporative losses, diffusion of $CO_2$ to the atmosphere, and requirement of large areas of land. Furthermore, contamination by viruses, fungi, predators and other fast growing heterotrophs have applied some restriction on the commercial production of algae in open culture systems to essentially only those organisms that can grow under extreme conditions. Also, due to low-efficient stirring mechanisms in open cultivation systems, their mass transfer rates may be very poor resulting in low biomass productivity.

The closed photobioreactors have different structures, such as airlift reactor, stirred reactor, flat panel or tubular reactor, which can be used for producing high value added products (such as medicinal or health products) or used as seed tank for open-pond cultivation, mainly due to very high costs (capital and operational).

Hybrid systems attempt to mix the best qualities of open and closed systems in order to achieve economic competitiveness. Usually, small closed systems grow a preferred algae species, which then seed a large open system. The higher fixed and operational costs of the closed system are kept to a minimum by keeping its relative size small, while the risk of environmental exposure of the open system is minimized by seeding it with sufficient amounts of algae from the closed system so that the preferred species dominates the pond.

Belgian Patent No. BE 1011897 describes algae cultivating devices comprising, inter alia, a support for holding angled transparent walls, gas and liquids inlets and reflectors. The devices can be connected to one another in series or parallel to form assemblies.

U.S. patent application Nos. 2008/0311649 and 2009/0215155, in the name of XL Renewables Inc. describe an apparatus for producing algae, the apparatus comprising flexible reactor tubing that has a wall that is at least partially translucent to sunlight; and a stationary circulation pump for moving algae fluid through the reactor tubing. The reactor tubing is made of clear polyethylene with UV inhibitors and preferably has a substantially circular cross-section that lies flat when not pressurized. Gas relief valves allow gases generated during algae production to escape from the reactor tubing. $CO_2$ may be injected into the algae fluid to stimulate photosynthesis.

International Patent Application Publication No. WO2004/008845 describes a culture tank comprising a receptacle for containing a culture medium and organisms to be cultured and substantially flat filter means arranged to filter particulate material from the culture medium; fluid motion imparting means arranged in use to introduce fluid into the receptacle such that the culture medium in the receptacle is urged to flow in a direction substantially parallel to the filter means so as to minimize collisions between organisms and the filter means; and additional means for urging the culture medium near the filter means to flow through the filter means.

Finally, U.S. Pat. No. 5,158,037 describes a device for aquaculture especially for raising fish, plankton and algae, with addition of oxygen-containing gas and nutrients, with aerating devices arranged in pools or ponds of a suitable shape and a gas through-put adjusted so that a bubble curtain is produced without major turbulence in the water of the pond. The bottom portion of the pools or ponds may be tilted towards the aerating device and the aerating device located at the deepest point of the pool/pond. As a result, the bottom is either flat or V- or multiple V-shaped, pyramidal or conical, with aerating devices located at the deepest point.

SUMMARY OF THE INVENTION

It is well appreciated that different aquatic organisms, such as algae can produce a variety of useful products. For example, the algae biomass enjoys a huge market potential for products such as Biofuels, energy production, high value products for pharmaceuticals, cosmetics, food additives, biochemicals and animal feed. For such purposes, various cultivating systems have been developed.

As described above, there are two main types of aquatic organisms cultivating systems: open ponds and closed photobioreactors (as well as hybrid solutions). Each type exhibits some advantages (or disadvantages) over the other. For example, the differences between the two types of systems may be in productivity as a function of volume, Biomass recovery and harvesting costs, process control (water loss, $CO_2$ loss, temperature), dependency on climate conditions, system's size and land resources, maintenance (e.g. cleaning), etc. In both cultivation systems, the harvesting is usually done either by centrifuge (high cost and energy) settling ponds, or both.

The present invention aims at providing an alternative system for cultivating aquatic organisms, such as, without being limited thereto, crustaceans, shrimps, worms, fish, fish larvae, planktonic organisms, gastropods, lemna, wolfia and in particular, algae, with a low energy harvesting, as it enables harvesting in the cultivating body (i.e. the container/pond where the organism are cultivated).

Specifically, a system has been developed by the inventors of the present inventions, which takes into consideration features of existing systems and incorporates them into a single, optimal, cultivating system.

More specifically, and in accordance with a first of its aspects, the present invention provides a system comprising a load-bearing structure having a top portion with at least two rims essentially transverse to each other and defining a top plane, and a bottom portion; a tank, at least a portion of which is flexible, and adapted for receiving therein a growing medium and for cultivating therein aquatic organisms, said tank comprising two or more sidewalls, each extending between a rim of the top portion and said bottom portion such that the tank is suspended within the load bearing structure, said two or more sidewalls extending such that at least in one cross section taken along a plane perpendicular to said top plane, at least two of the sidewalls form a substantially or essentially V-shape converging towards said bottom portion; the system further comprising a gas emitting arrangement linkable to a source of pressurized gas and comprising at least one gas emitting nozzle disposed within the tank, preferably at said bottom portion.

The present invention also provides, in accordance with another aspect, an arrangement for cultivating aquatic organisms comprising two or more systems as defined herein, to form a cultivating plant/farm.

The aquatic organism to be cultivated in the system disclosed herein may be any known photosynthetic microorganism. When referring to photosynthetic microorganisms, any known species of oxygen releasing organism and algae may be grown in the system disclosed herein. These include, without being limited thereto, *Nannochloropsis* sp., *Nannochloropsis salina*, *Nannochloris* sp., *Chlorella salina*, *Dunaliella tertiolecta*, *Dunaliella salina*, *Isochrysis* sp., *Isochrysis galbana*, *Tetraselmis suecica*, *Tetraselmis chuii*, *Phaeodactylum tricornutum*, *Coccomyxa* sp. The various microorganisms may be grown separately or as a mixture of aquatic organisms.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 4 is a schematic illustration of a sheet material foldable into a cultivating tank in accordance with one embodiment of the invention.

FIG. 10B shows culture pH when cultivating *Coccomyxa* sp. The pH was monitored daily and corrected by controlled $CO_2$ flux, FIG. 10C showing Cell density and chlorophyll levels when *Coccomyxa* sp. was inoculated in the system of the invention, cell density and chlorophyll levels were measured at OD (Optical Density) 750 and 680 nm respectively.

DETAILED DESCRIPTION OF SOME NON-LIMITING EMBODIMENTS

Figure 1:
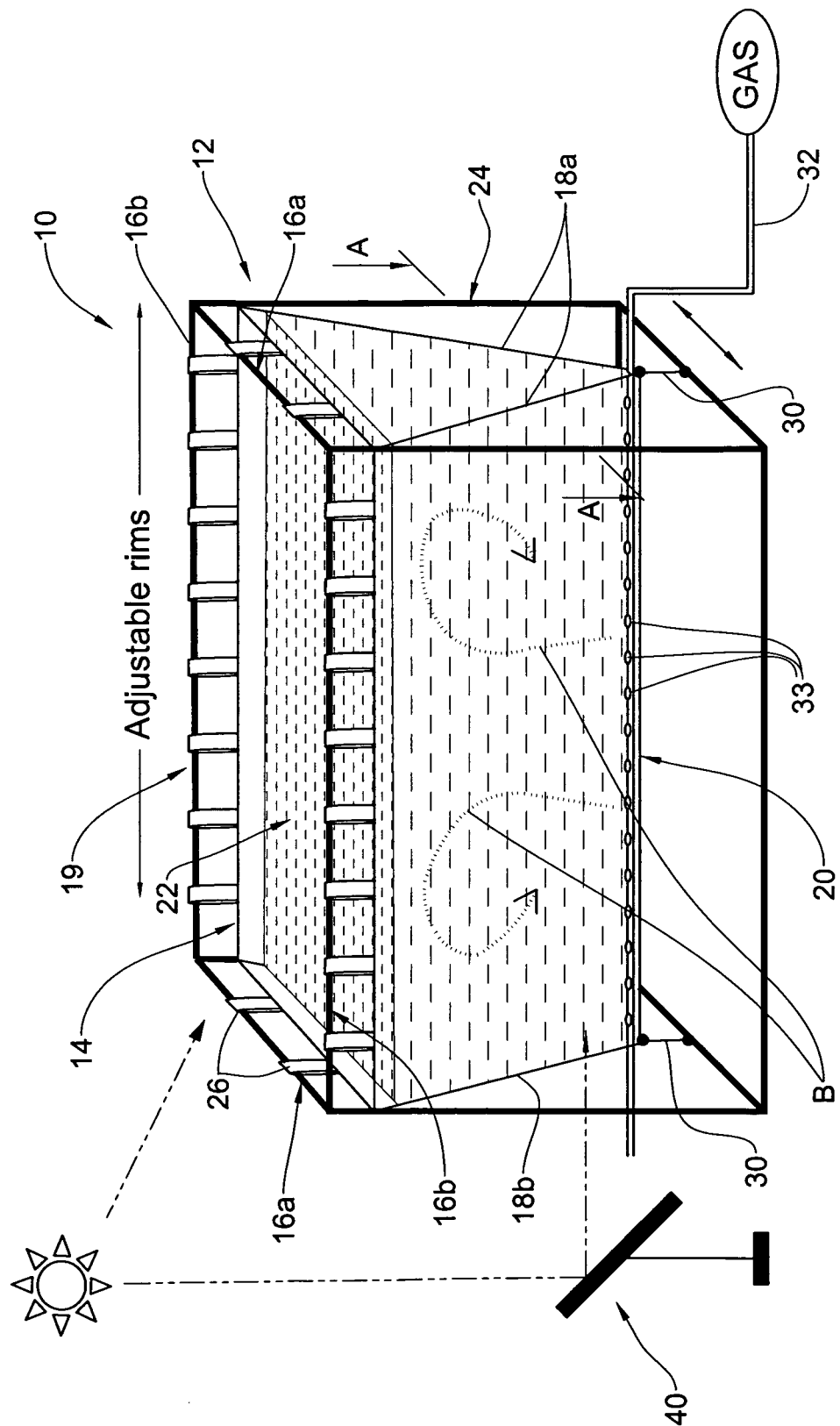
FIG. 1 is a schematic illustration of a cultivating system according to an embodiment of the invention.

Closed-system bioreactors (vertical-column, flat plate, tubular etc.) are well recognized for their excellent ability to control sterility as well as all growth effecting parameters like temperature, pH, light intensity and duration, $O_2/CO_2$, and nutrients concentration. In doing so these systems permit continues cultivation of a wide variety of species. However their application to industrial production is limited to small scale and to high capital costs.

Open pond technology and particularly raceway shallow ponds have advanced to affordable industrial scale growing systems, but are limited in their providence of sustainable production and to a selected number of strains that may be grown in such systems. The open ponds are characterized by poor light utilization by the cells, high evaporative losses, fast diffusion of $CO_2$ to the atmosphere, requirement of large areas of land due to low culturing volumes, contamination by predators and other fast growing algae, low biomass productivity compared to closed bioreactors, energy-intensive harvesting by centrifuges and use of settling ponds.

The present disclosure is aimed at providing a system for cultivating aquatic organisms that presents capital expenditures (CAPEX) and operational expenditures (OPEX) in the costs range of open ponds, with higher biomass productivity per volume and less need for land resources.

As will be evident from the following, the system disclosed herein allows a controlled environment (exposure to light, contaminations, stable pH and $CO_2$ supply) due to its unique construction and thus provides a tool for cultivating a wide variety of microorganisms, including unialgae cultures, oligenus or exotic algae.

In line with the above, the inventors have developed a cultivating system that comprises a load-bearing structure that carries a culture tank, at least a portion of which is flexible. The load-bearing structure has a top portion with at least two top rims transverse to each other defining a top plane. The load bearing structure also has a bottom portion.

The tank that is adapted to receive a growing medium and aquatic organism(s) comprises two or more side-walls, each extending between a rim of the top portion and said bottom portion such that the tank is suspended within the load bearing structure. Further characterizing the tank are the two or more extending side-walls having a cross section, when taken along a plane perpendicular to the top plane that forms a general V-shape, converging towards the bottom portion. Such V-shape forming sidewalls are referred to herein, at times, as the "slanted sidewalls". The side-walls extend down from the top rims to a bottom portion of the tank.

The system also comprises a gas emitting arrangement that is linkable to a source of pressurized gas, which comprises gas-emitting nozzles that are disposed within the tank at the bottom portion.

The load-bearing structure holding the culture tank typically define a parallelepiped with two essentially parallel top rims. The top rims also define the length of the parallelepiped.

In some embodiments, the side-walls extend down from the top rims to the tank's bottom midline. As noted above, when the tank is filled with fluid, e.g. growing medium, the side-walls may adopt some degree of curvature due to the weight of the fluid causing pressure on the walls, albeit while maintaining the essentially V-shape structure.

In accordance with one embodiment, particularly suitable for cultivating algae, at least some side-walls, particularly the slanted sidewalls, are transparent or translucent allowing light to pass through the walls.

In the context of the invention, when referring to transparency or translucency (semi transparent), it is meant that at least 75%, even 85%, further even 90% and at times even 95% of the light that reaches the side wall of the tank is transmitted therethrough. In this connection, it is noted that the V-shape system allows light to be transmitted even at the internal space at the bottom end of the system. In fact, 10% or even 15% light reaches the organisms via the sidewalls, at the bottom end of the V-shape structure (in addition to the light received from the top portion of the system).

Portions of the tank are flexible, at least to the extent allowing folding (bending) or any other form of re-arrangement or configuration of the sidewalls of the tank to a desired configuration, the desired configuration typically dictated by the shape of the load bearing structure. In some embodiments, the flexibility may be characterized by its resistance to deformation (i.e. tensile modulus). The ability of the material to resist deformation is understood as the ratio of stress caused by the growing medium on the sidewalls of the tank to the amount of deformation of the flexible portions of the material forming the sidewalls). The tensile modulus may be defined as the ratio of stress applied to the elongation, which results from the stress.

In accordance with the invention the walls of the tank may be formed from various materials, characterized by the following tensile modulus:

| Material | GPa (Giga Pascal) | psi |
| --- | --- | --- |
| HDPE (High Density Polyethylene) | 0.8 | |
| PP (Polypropylene) | 1.5-2 | 217,000-290,000 |
| PET (Polyethylene Terephalate) | 2-2.7 | |
| Fiberglass (GRP) Polyester | 17.2 | 2,500,000 |
| Fiberglass (GRP) | 40-45 | 5,800,000-6,500,000 |
| Glass | 50-90 | |
| Polyethylene (woven sheet) | n/a | |
| PVC (polyvinylchloride) | n/a | |

The properties of the material forming the tank may affect the type of the supporting structure. Needless to note, a structural robustness sidewalls may reduce costs and complexity in the construction of the support structure.

In some embodiments, the walls of the tank are plastic materials.

In some more specific embodiments, the walls of the tank are synthetic polymers selected from any one of the following non-limiting examples: high density polyethylene (HDPE) woven sheet coated with low density polyethylene (LDPE), the coating typically assists in making the woven HDPE impenetrable/impermeable to water; Polypropylene woven sheet, also coated, for water impermeability; polyolefin woven materials, such as ethylene Vinyl Acetate (EVA), LDPE, polyvinyl alcohol (PVA), coated with an water impermble layer; biaxially orientated Nylon (BON); polyethylene terepthalate (PET); biaxially orientated polyproplene (BOPP) film; low density polyethylene (LDPE); linear Low density polyethylene (C4 LLDPE); metallocene catalysed polyolefin plastomer (Hexene or Octene) polyvinylchloride (PVC).

In some embodiments, at least a portion of the sidewalls comprise a coated woven polyethylene sheet that is impermeable to water and is characterized by the following physical parameters:
Weight: 140-200 gr/m$^2$;
Breaking strength: 12-20 kg/cm;
Tear strength: 12-20 kg;
Light transmission 80%-95% (UV protected)

One example of interest in accordance with the invention is the commercially available product, Solaroof, which is a two sided coated woven polyethylene sheet that is available from Pic Plast Ltd. (Moshav Merchavia, Israel) or from Nayer Bros. (Elkana Industrial Zone, Israel).

The material forming the walls may be provided as long rolled sheets, already in the desired width (e.g. up to 3 m (twice W in FIG. 7)), to be cut according to the length (L in FIG. 7).

In some other embodiments, and in order to maintain the general V-shape of the system, at least the slanted walls of the tank are either rigid or are supported by the rigid load bearing structure, to an extent required to essentially maintain said V-shape.

The V-shape at the bottom portion of the device was found to be essential for various reasons:
Mixing of the culture inside the medium is achieved by air bubbles rising upwards from the pipe nozzles positioned at the bottom of the V-shape. This mixing in the V shape did not allow any sedimentation of cultured cells at the bottom since they were pushed upwards immediately. It is noted that in U shape systems, the cells would sediment on the far side of bottom of the U shape.
For harvesting using flocculation in the same cultivation system, soon after flocculation cells sediment at the bottom of the system and condense over time into the lower part of the V shape. Harvesting in the V shape structure resulted in a smaller volume of sedimentation area compared to a larger system or compared to U shape systems
The V-shape allows the concentration of the cultured organism at the bottom portion, essentially with no or minimal adherence to the sidewalls, a phenomena that would occur when the sidewalls are curved, e.g. in a U-shape system. Adherence of the cultured organisms to the sidewalls reduces yield significantly.
The V-shape supports flocculation, nutrient depletion, different environmental stresses, and supports conditions to enhance lipid production and also supports culturing of uni-alga cultures or multiple algae species cultured simultaneously.

The two or more top rims of the parallelepiped may be configured to be adjustable in length. As will be described hereinafter, there is a variety of means enabling the adjustability of the rims. Manipulation in length of any two essentially parallel rims affords, inter alia, tilting of sidewalls in the system and thus adjusting the system to external environment and better control of the cultivation conditions.

In accordance with an embodiment of the invention, the load bearing structure comprises legs that carry the top rims. In some embodiments, the top rim forms a top frame bordering the top plane, with the tank being carried on said frame. At times, the legs and the top frame have a generally prismatic structure and comprise a base (bottom) frame that connects the legs at their bottom end. The base frame may be adjustable in size similar to the top frame carrying the tank. The legs and the frames are typically made of a material that is capable of holding the load of the tank when filled with fluid such as growing medium for aquatic organisms.

Turning now to FIG. 1 there is illustrated a system 10 in accordance with a non-limiting embodiment of the invention. While the system 10 is described with respect to cultivation of algae, it is to be understood that this is done for simplification only and the same construction may be utilized for cultivating other aquatic organisms, particularly, organisms that depend on or require light for cultivation.

System 10 comprises a load bearing structure 12 defining a parallelepiped (in this particular embodiment, a rectangular parallelepiped) and a flexible culture tank 14, the load bearing structure 12 having two sets of opposing essentially parallel top rims 16a and 16b that carry the flexible culture tank 14. The tank 14 has a general V-shaped defined by a pair of slanted sidewalls 18a (only one marked in FIG. 1) extending down from said paralleled top rims 16b to a bottom portion 20 of the tank 14. In this particular example, the pair slanted sidewalls 18a meet at the midline bottom end of the system 10 and extend between another pair of essentially parallel sidewalls 18b (only one marked in FIG. 1). Sidewalls 18b (with only one illustrated) are essentially vertical walls, albeit, are not limited to such orientation. The total four sidewalls define the system's top opening 19, bottom portion 20, and an internal space 22, the latter for receiving the tank 14 and holding therein the culturing medium and cultivated organism.

The two slanted sidewalls 18a have a generally triangular shape and the other two parallel sidewalls 18b have a generally rectangle shape. Nevertheless, it is to be appreciated that the tank's walls may also have a shape forming an inverted pyramid, where all four walls of the tank are slanted such that they meet at the tank's bottom center. Further, in some embodiments, the tank may have a generally conical shape. To this end, the top rims are connected together to adopt circular or ellipsoid shape with an adjustable diameter.

As shown in FIG. 1, the tank 14 is held by the top rims forming together a top frame using in this particular embodiment hanging loops 26 fitted over the top rims, but similarly may also be held using bents or hooks or weights hanging over the top rim or by folding and welding the top edges of the sidewalls over the top rims to form a sleeve-like attachment, or by any other fastening equipment or technique for fastening the sheet or other material forming the tank.

The tank 14 may also be connected to bottom anchors 30 that may be adjustable in length and/or position (or replaced by other anchors of different lengths). The anchors 30 may be used to stretch/pull down parts of the tank so as to assist in maintaining the V-shape of the tank, e.g. when filled with fluid. The anchors 30 may be connected to the bottom portion of the load bearing structure or the downward stretching may be achieved using weights.

Figure 2:
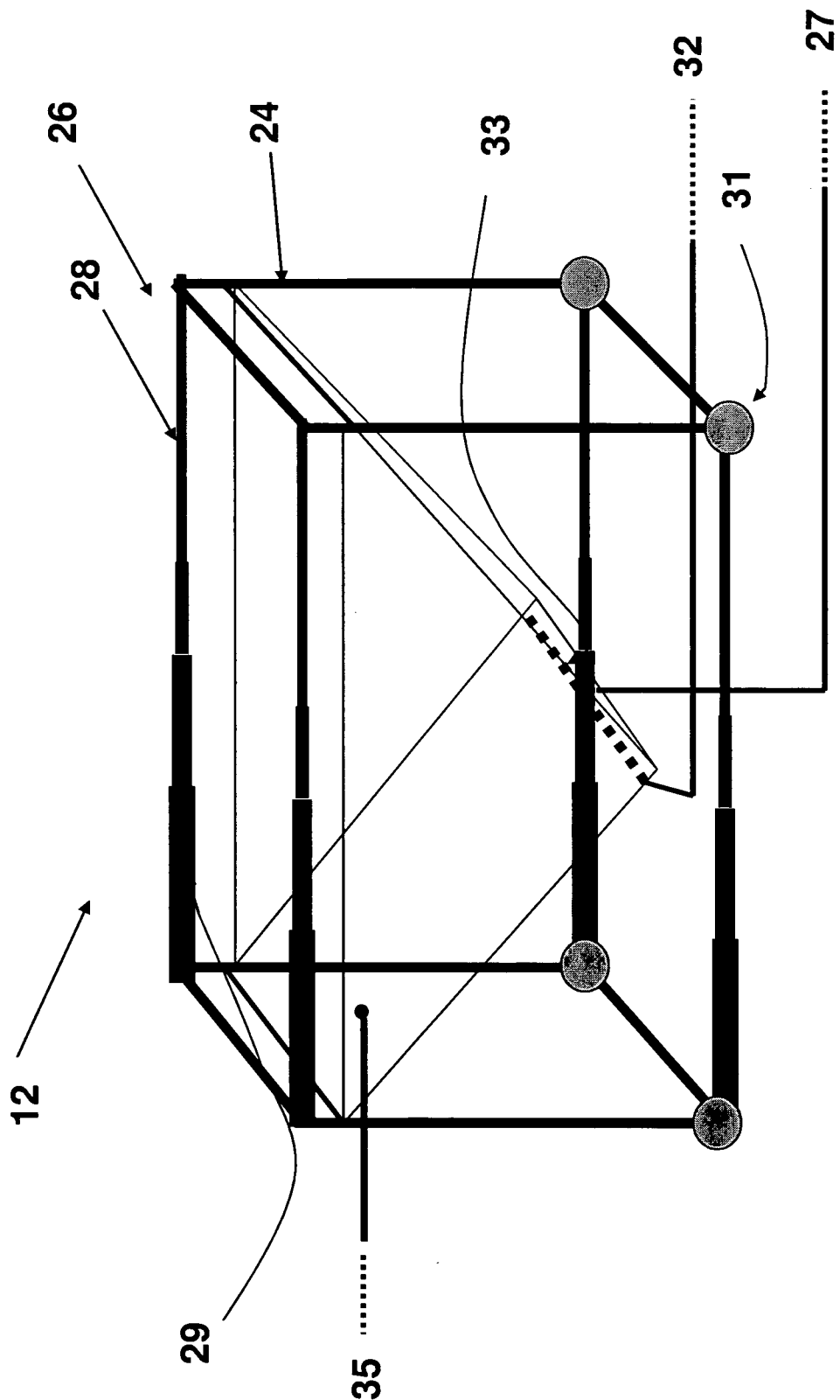
FIG. 2 is a schematic illustration of a load bearing structure according to an embodiment of the invention.

A schematic illustration of the load bearing structure 12 is also provided in FIG. 2. The load bearing structure 12 has the legs 24 and length adjustable top rims 28 forming a top frame carried on said legs. Further, the load bearing structure 12 has a bottom frame 27 at a bottom portion of the load bearing structure 12. The top rims 28 and top frame 26 and the parallel bottom frame are configured to have at least two parallel rims adjustable in length, which are also parallel to the tank's length-adjustable bottom frame, or by replacing one or more rims with one or more other rims of a different length (shorter or longer). Similarly, the length of the vertical legs 24 may be adjusted (not shown).

The load bearing structure 12 may also have modular rims, illustrated in FIG. 2 as telescopic elements 29 which may be elongated or shortened, according to the desired dimensions. Alternatively, modularity may be achieved using build up (inter-connected) parts, for building rims with desired length. To this end, the rims may have fixed ends, at rim connecting elements 31, located for example at the point of connection between the legs 14 and the bottom frame, and build up sections, connecting the fixed ends (not shown), thus allowing to expand the size & volume of each tank.

System 10 illustrated in FIG. 1 also comprises a gas emitting arrangement 32 linkable to a source of pressurized gas (not illustrated) and in fluid communication with the tank such that gas is emitted from gas emitting nozzles 33 disposed, preferably, at the bottom section 20 of the tank 14, essentially, in parallel to the slanted side wall.

The gas emitting arrangement 32 is configured to introduce a supply of at least carbon dioxide ($CO_2$), oxygen ($O_2$) and/or air. When the gas is air, the air may be a combination of $CO_2$ with compressed air at a certain percentage and to this end may be air, even air pumped from the external surrounding. In addition, the gas emitting arrangement, by introducing gas such as compressed air into the culturing medium, provides turbulence and mixing of the fluid in the tank and flow of the matter from the nozzle's area, inter alia, to prevent sedimentation of the organism at the bottom V-shape end of the tank. Without being bound by theory, it is assumed that using nozzles in a configuration as illustrated in FIG. 1, i.e. at the bottom end of the slanted walls, the gas forces flow of the biomass in the tank upwardly, in a direction as illustrated in FIG. 1 by arrows B, thereby providing even distribution of the cultivated algae in the tank 14. The above should not be construed as limited the positioning of the gas emitting nozzles at any other location in the tank, such as midway between the bottom end and top end of the tank, as long as the location provides an amount of turbulence at the slanted sidewalls, to prevent formation of sedimentation.

The gas emitting arrangement may be made of any suitable air tubing/piping, including flexible or rigid plastic, such as silicon or PVC tubing, pipes used for irrigation or metal such as stainless steel. The gas arrangement may use pumps and/or blowers to pump air from the environment, preferably via the use of microfilters to avoid contamination.

In case the sidewalls are high (for example, 2 meters from the bottom level of the tank), a second gas emitting line may be introduced, for example, halfway between the top and bottom of the tank to enhance culture mixing (not illustrated). The nozzles may have defined diameters (e.g. between 0.1-2.0 mm) and be set at certain distances (e.g. 10~50 mm apart). The dimensions and distribution of the gas emitting nozzles in the tank will depend, inter alia, on the dimensions of the tank (e.g. width), and the pressure of the gas and can be optimized upon construction of the system.

Carbon dioxide can be blended with compressed air at a certain percentage (for example from 0.1 percent up to 10% or even 15% of $CO_2$) to provide carbon source for photosynthesis. In some cases, organic carbon (for example, in the form of acetic acid and/or glucose) can be added as needed into the culture medium to support growth. Any suitable source of carbon dioxide can be used, including but not limited to industrial grade, food grade, filtered $CO_2$-rich flue gases emitted from power generators burning coal, biomass (including algal biomass and/or biomass residues after high-value products are extracted), natural gas, biogas (e.g., ethanol, methane obtained from anaerobic digestion/fermentation of algal biomass or biomass residues and/or from anaerobic digestion of organic waste), and liquid fossil fuel or Biofuels (including algae-based biodiesel).

The system 10 may also include a light reflecting element 40, as illustrated in FIG. 1, configured to reflect light at least onto the slanted sidewalls. The light reflecting element 40 may be in the form of a mirror so as to redirect light from the surrounding of the tank onto the transparent walls and thereby increase the illumination of the internal space of the tank.

To further increase exposure of the aquatic organism to light, the system 10 may be provided with a light emitting elements that may be located above the tank's top opening, be integrally formed with a tank's cover (as described below), or be at least partially submerged in the liquid medium holding the algae. The introduction of artificial light emitting elements is utilized to increase productivity, e.g. by illuminating the liquid's top surface to compensate periods of limited natural light availability, e.g. during night time or during hours where the natural light source is insufficient. The use of artificial light emitting elements may also allow utilization of the system for indoor algal cultivation. The artificial illumination can be provided in the form of fluorescence tubes, incandescent tubes, mercury vapor lights, light emitting diodes, LED's and the like.

The system 10 may also contain at least one inlet port 35, as illustrated in FIG. 2, in fluid communication with the tank 14, for introducing fluid, including but not limited to culture medium, algal suspensions, water/wastewater, and nutrient solutions, into the tank. In one embodiment, the inlet port is located near a top edge of a tank's side wall. There can be one or more inlet ports to deliver culture medium, algal suspensions, water/wastewater, or nutrient solutions. Different solutions can also enter the tank through a single inlet. Different nutrient concentrations affect the growth and biochemical composition of algal cells. For example, nutrient-rich medium may stimulate and sustain high growth rate and biomass productivity, whereas nutrient depleted medium may stimulate biosynthesis and cellular accumulation of neutral lipids, long chain fatty acids, and/or secondary carotenoids. A nutrient gradient created in a tank may allow a continuous shifting of algae from a high biomass production mode to a high accumulation of specific desired product mode (e.g. high-lipids content).

Alternatively, multiple inlets ports may be located at certain distance apart from one another to ensure nutrient and/or algal cell concentrations to be more or less homogenous throughout the tank. In this case, the cells grown in a given tank or in compartments of the tank (as will be discussed below) will have identical, desirable physiological status for specific applications. The distance between inlets ports can be optimized for a given use. The inlet port(s) can be located at any height relative to the sidewalls or struts.

The system 10 may also comprise at least one outlet port 27, also as shown in FIG. 2, for removing fluid from the tank, including culture suspension for harvesting. In one embodiment, the at least one outlet port is located at the bottom section of the tank 10 and is equipped with a controllable valve, e.g. a solenoid valve-mediated outlet, that can be automatically or manually opened or closed upon need. Thus, the outlet port, when located at the bottom section of the tank will serve for both harvesting and drainage (to facilitate draining of water/culture with minimum energy requirement. Normally, there will be a single drainage outlet per cultivating system. However, for a system of extended length, multiple drainage outlets may be preferred.

Inlet port(s) are connected to a growth medium supplying tank (not illustrated) that provides fresh growth medium upon need; and outlet port(s) are connected to a receiving container that collects liquid suspension containing the algae drained from the system.

Figure 3A:
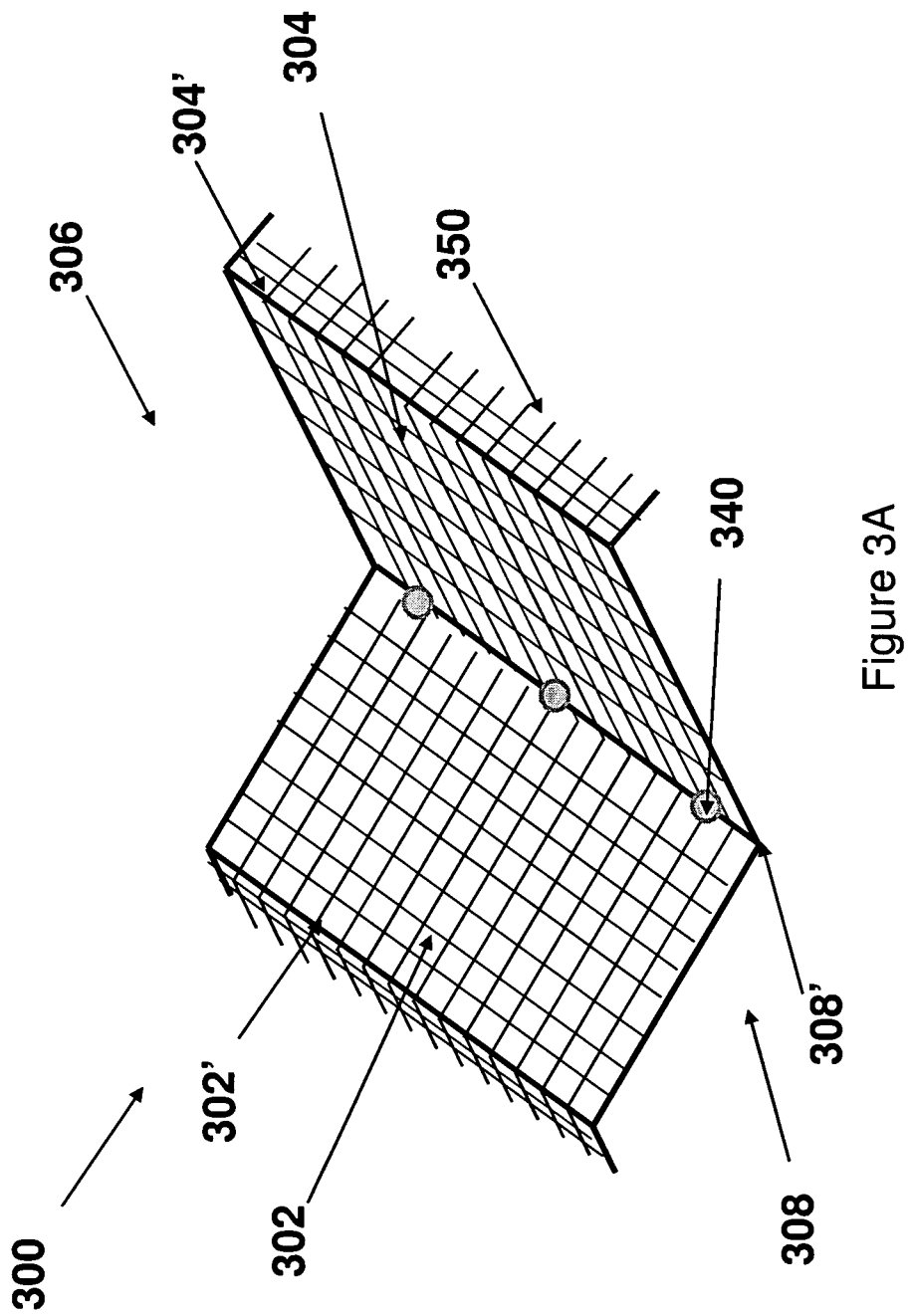
FIGS. 3A-3B are schematic illustrations of a system comprising a supporting structure in accordance with some embodiments of the invention.
Figure 3B:
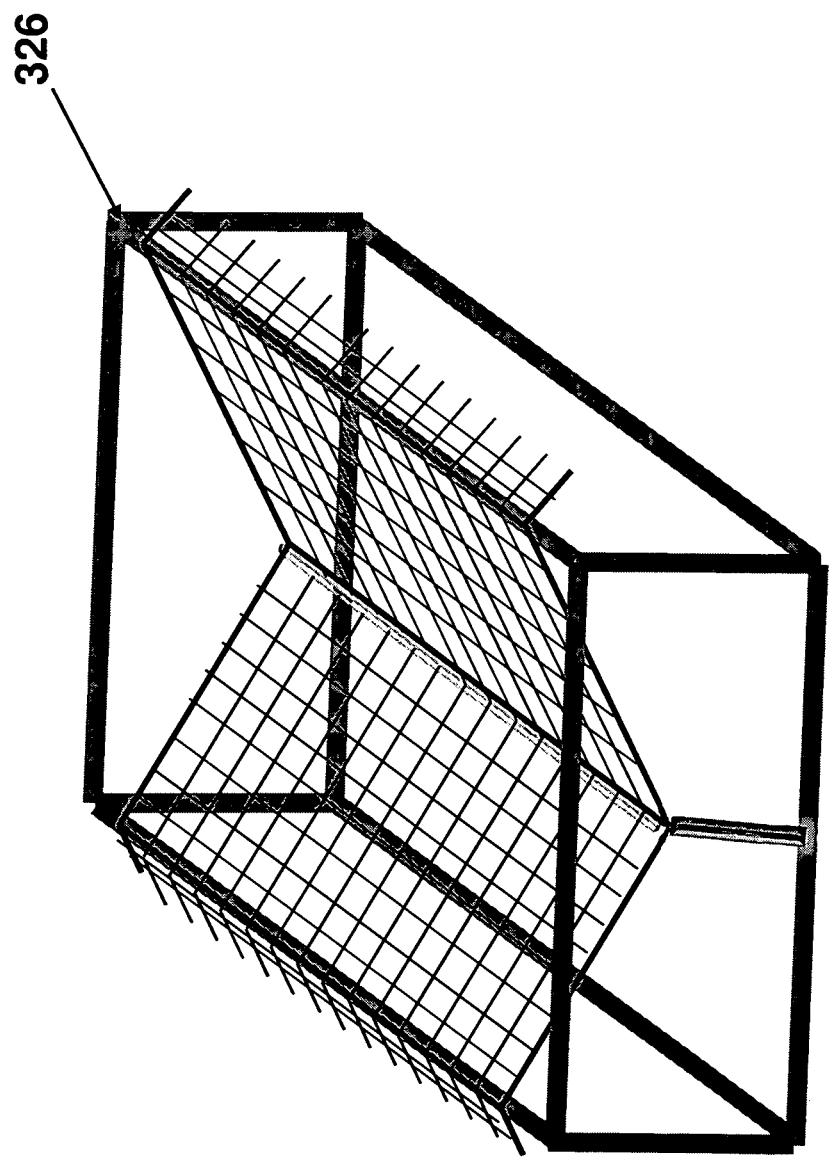

In an alternative embodiment, the V-shape configuration may be provided using a V-shaped supporting device/carrier made of a rigid material, adapted to hold the flexible tank. In this connection, reference is made to FIGS. 3A-3B illustrating an exemplary embodiment of a supporting structure 300. FIG. 3A shows a gridded (net-like) structure 300 formed of two parallel gridded carrier walls 302 and 304, having a top portion 306 defined by top ends 302' and 304' of the two carrier sidewalls 302 and 304 and a bottom portion 308, where the two walls 302 and 304 are connected at a bottom end 308' (or simply folded as illustrated). The grid carrier 300 is equipped with top flaps 350 at top ends 302' and 304' for hanging over the top frame 326 of the load bearing structure 312, as illustrated in FIG. 3B. The carrier 300 is preferably made of a rigid material that allows maintaining the V-shape structure of the flexible tank when the latter holds culturing medium and aquatic organisms therein. Without being limited thereto, the carrier 300 may be made of any robust material, such as galvanized steel, stainless steel and alike and may be in the form of a mesh or net to form the gridded structure of the carrier 300.

The carrier 300 may include hinges 340 connecting the two carrier sidewalls 302 and 304. These hinges may allow tilting of the carrier's sidewalls upon need and in line with the adjustments made in the dimensions of the load bearing structure 12.

When in gridded form, light is transmitted through the gaps and through the tank into the tank's void. The grids may be symmetrical or asymmetrical and have any desired dimension. As an alternative for a net like carrier, one may use perforated plates, the light being transmitted via the perforations (holes).

In accordance with a preferred embodiment, at least some sidewalls, particularly the slanted sidewalls, are transparent or translucent (semi transparent). When the system is used for algal growth outdoors, these transparent or translucent sidewalls face the sun or any reflector (e.g. mirror, white material, foil and alike). The transparent or translucent sidewalls of the tank can be made of any transparent or translucent material, which is also (100%) water impermeable, some examples of which are provided hereinabove. When transparency (at least 80% light transmission) is required, some sidewalls may be made of a rigid material and some from a flexible material. Without being limited thereto, the sidewalls may be of glass or fiberglass (when not required to be flexible) or from flexible, transparent and water impermeable plastic sheets. In some embodiments, the sidewalls are at least partially UV protected.

Figure 5B:
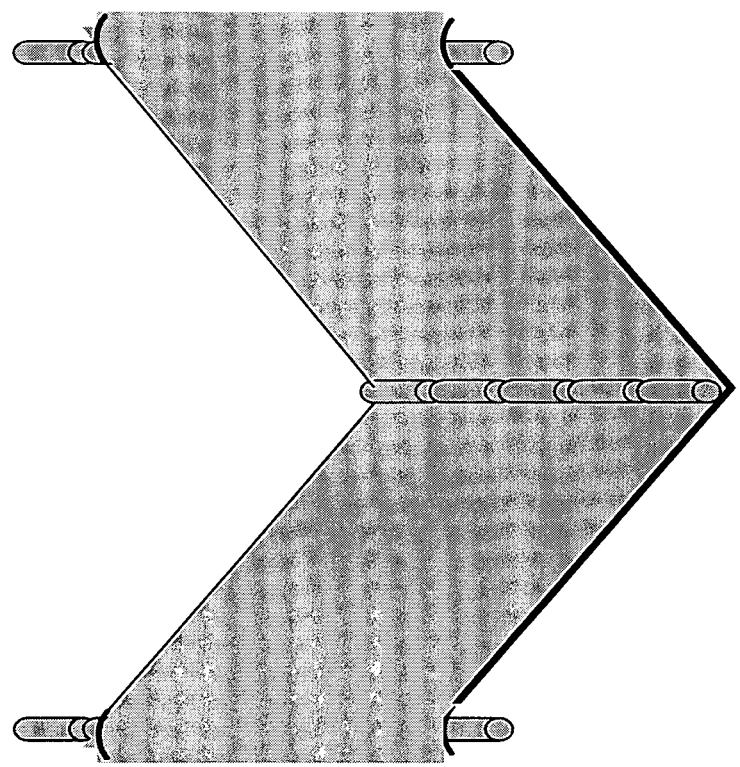
FIGS. 5A-5B provide an example of a single sheet (FIG. 5A) that may be cut to a desired dimension and placed onto a load bearing structure to form the desired V-shape (FIG. 5B).
Figure 5A:
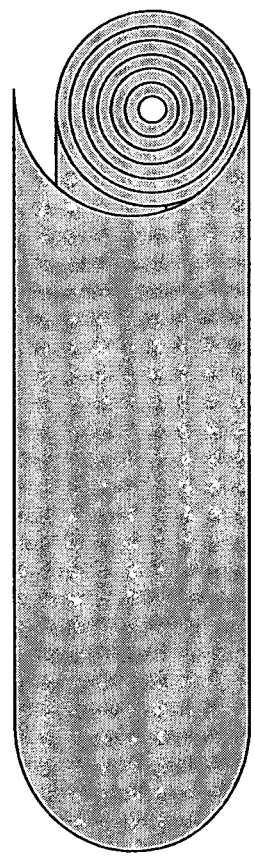

The material forming the sidewalls may be connected to each other by any suitable techniques, including welding, adhesion, mechanical connection (clamps) or by molding, e.g. using plastic extrusion technology. In some embodiments, the tank is made of a single sheet of flexible material that is folded into the desired arrangement, as illustrated in FIGS. 4 and 5A-5B. In some embodiments the sheet is provided as a long rolled sheet, the width of the sheet being in the width of the two sidewalls of the tank (2×W, folded in its half width for forming the sidewalls of the V-shape) and stretched along the length (L) of the tank.

The tank may be disposable or reusable tank. When reusable, harvesting may be performed either when still within the load bearing structure, e.g. via a dedicated outlet, or after the culturing media is removed (without the cultured organisms) after which the tank may be released from the load bearing structure (e.g. by gently pulling over the top rims) for either collecting the cultured organism, drying, washing, disinfecting or any other desired treatment, prior to re-using.

In some embodiments, the tank is made of a single sheet which is removed from the load bearing structure for spreading out and allowing the cultured organisms to dry in the open air.

The transparency of at least a portion of the sidewalls is advantageous in order to allow light to pass through the walls into the interior volume of the tank. In such cases, where light transmission and light absorption by the aquatic organism is essential for productivity, particularly for high yield (commercial level) production, the system may further be equipped with light reflecting elements, as further discussed below that are configured to reflect light onto at least the slanted sidewalls. In accordance with another embodiment, the system comprises light emitting elements that are configured to emit light onto to the slanted sidewalls, typically from the exterior side of the system so as to transmit light into the tank.

The dimensions of cultivating tank may vary and will depend, inter alia, on the type of aquatic organism to be cultivated therein, the desired amount of biomass, the desired volume, environmental conditions such as the altitude, temperature, light intensity, radiation, climate etc., commercial intended use and area limitations etc.

In some embodiment, the depth of a tank may be between 25 cm to 2 m, and preferably between 50 cm to 2 m from the top surface of the liquid contained in the tank and the depth will depend on the length of the tank, which may be, for example, 1 meter long. Without being bound by theory, it is postulated that the use of slanted walls as in the present system, and the transparency of part or all the walls, permits growth of aquatic organisms, such as microalgae at depths from the upper surface of the growing medium when within the tank, which are not applicable with commercially available open ponds. For example, commercial raceways are characterized by a growing depth of about 15-25 cm (as compared to the above depths defined with respect to the system disclosed herein). As appreciated, the possibility to work in depth, as in the system of the present invention, reduces the amount of land resources required for growing a volume of organism as compared to the same volume grown by commercial raceways.

Figure 6A:
FIGS. 6A-6C are schematic illustrations of three different angles that can be formed by the slanted sidewalls of a cultivating tank in accordance with some embodiments of the invention.
Figure 6B:
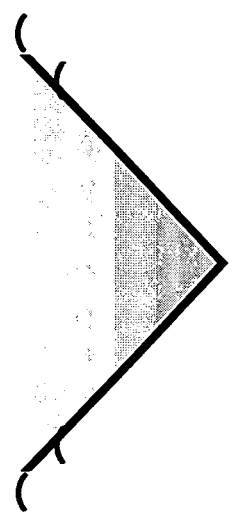
Figure 6C:
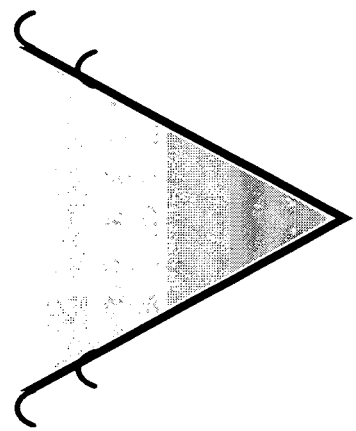

The sidewalls may be slanted by any means available in the art and the angle between the slanted walls may be in correlation with the amount of solar energy to which the interior of tank is exposed. A direct relationship between solar energy and productivity is observed: the higher the amount of solar energy admitted via the top surface, by increasing the sidewall's tilt angle, the higher the productivity (e.g. viable organism amount) sustained in the culture. The sidewalls tilt angle exerts an effect on the optimal population density and thus on the productivity of cell mass, due to its effect on the amount of solar radiation impinging on the walls of the tank. A benefit in orientating and tilting the sidewalls at various angles to the sun both daily and throughout the year is to reap the maximal potential associated with the biological conversion of solar energy. Frequent adjustment for the optimal sidewalls angle throughout the year will result in the highest overall annual productivity. The tilting of the sidewalls allows manipulation of the exposure to light. For instance, deficiency in light results in increasing the angle formed between the two slanted sidewalls (FIG. 6A) so as to increase the surface area of the culture medium while high exposure to light necessitates decreasing the angle between the slanted sidewalls, so as to decrease the surface area of the culture medium (see FIG. 6C).

Generally, it has been found in studies that up to 40 percent enhancement in annual biomass yield may be achieved by optimal manipulations of such angles in known algal cultivating systems. The angel between the two slanted walls of the tank 14 and, if needed, of the carrier 300 may be adjusted every several hours, every several days, every several weeks etc., it would however typically be fixed per growing cycle. A growing cycle, in this context is defined by the concentration of organism cultivated, i.e. a cycle may be completed once the concentration in the tank or the compartment reaches a desired range.

The angle may affect the amount of biomass adhereing to the inner surface of the sidewalls. Typically, the larger the angle (e.g. above 90°), the more biomass adheres to the inner surface of the sidewalls.

Figure 7A:
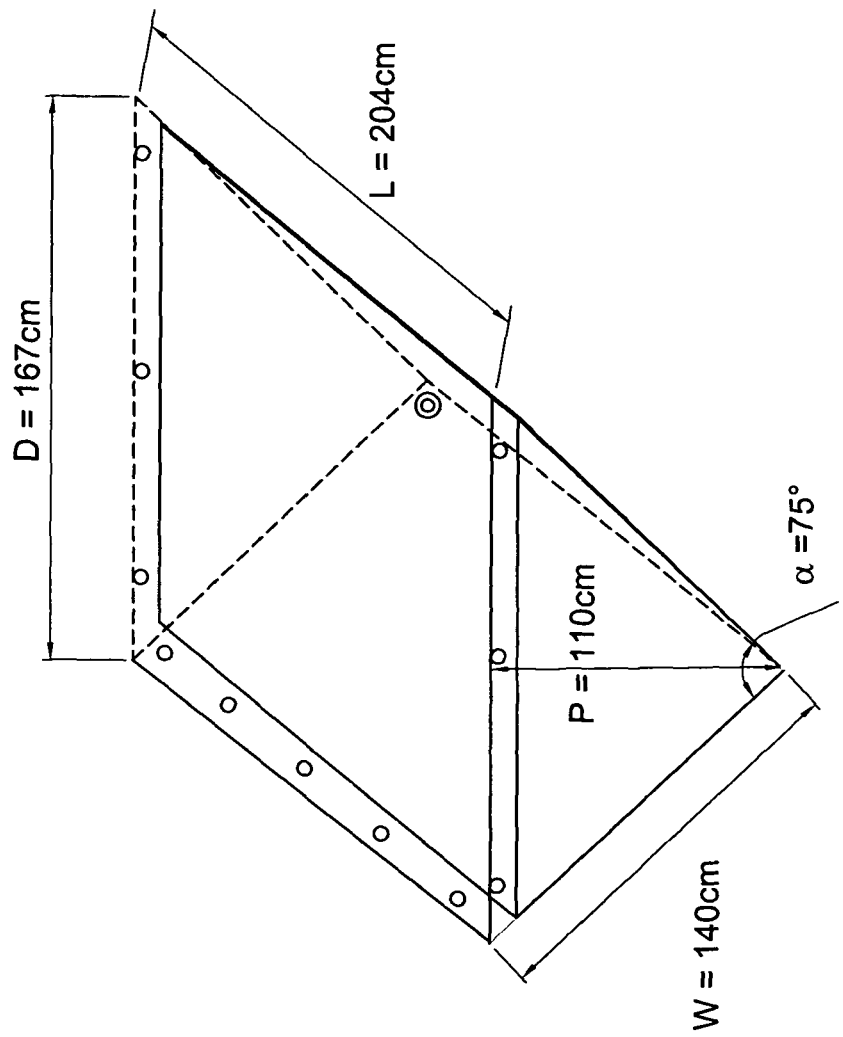
FIGS. 7A-7D show parameters defining dimensions (FIG. 7A and FIG. 7B), as well as corresponding images (FIG. 7C and FIG. 7D) of two alternative tanks in accordance with two non-limiting embodiments of the invention.
Figure 7B:
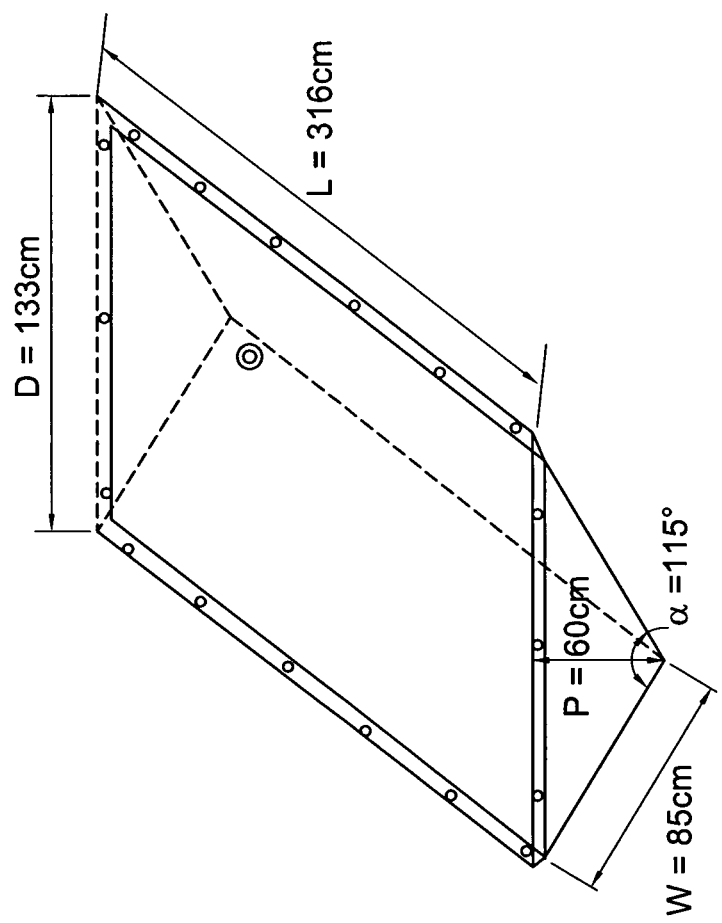
Figure 7C:
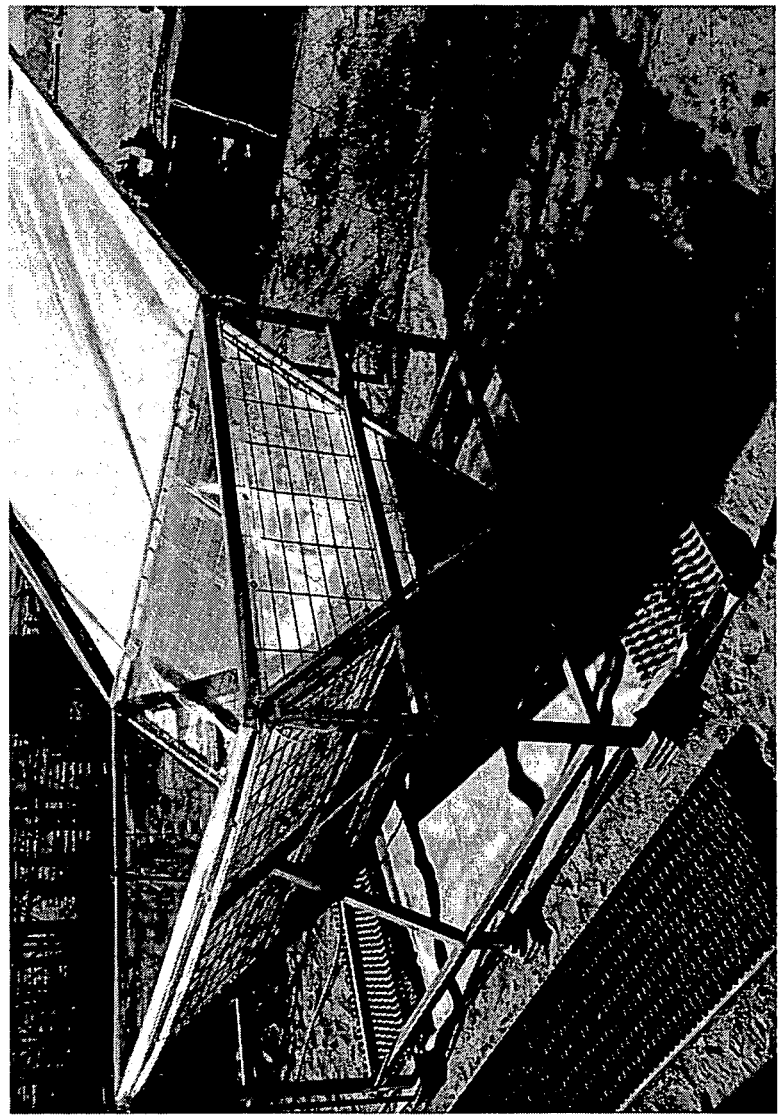
Figure 7D:
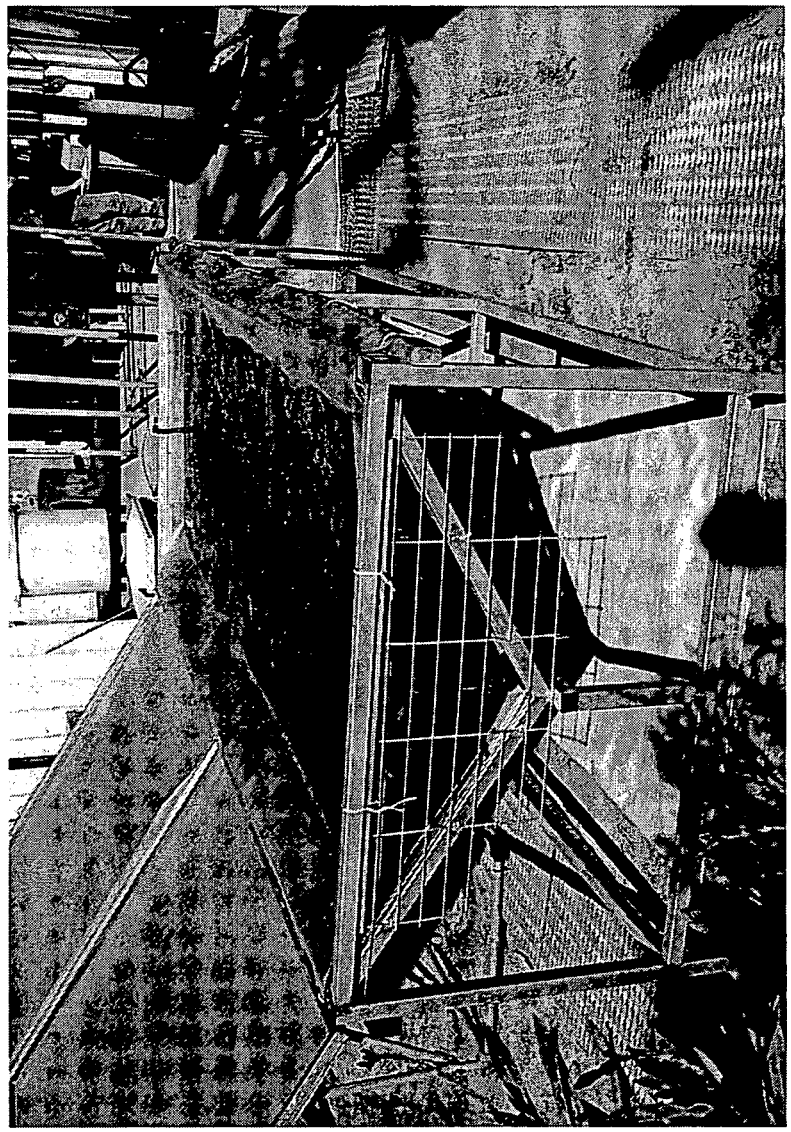

In addition, the angle dictates the dimensions of the tank, and thereby its volume and required area. For example, for 1,500 liter of growing medium, and an angle ($\alpha$) of 75° between the sidewalls, optimal minimal tank for production of algae may require a tank's length (L) of 204 cm, distance (D) of 167 cm from one side wall to the other, at the top ends, a depth (P) from the top surface to bottom end of 110 cm and side wall's width of 140 cm (FIGS. 7A, 7C). In some other embodiments, for 500 liters of growing medium, and an angle ($\alpha$) of 115° between the sidewalls, optimal minimal tank for production may require a tank's length (L) of 316 cm, distance (D) of 133 cm from one side wall to the other, at the top ends, a depth (P) of 60 cm and side wall width of 85 cm (FIGS. 7B, 7D). Ideally, however, without being limited thereto, the angle between the sidewalls is between 60° to 120°, preferably between 70° and 110° and more preferably between 85° and 95°. In one particular embodiment, the angle is about 90°.

The system may also include one or more partition members extending upwardly from the bottom to the tank's upper end and between two essentially parallel sidewalls (not illustrated), so as to define two or more inner compartments within a single tank. In some embodiments, a partition member may generally transverse the tank's bottom midline (extending between the two slanted walls) so as to divide the tank into two, compartments, that may be equal or different in size. In some other embodiments, the one or more partition members may be utilized to divide the tank into several compartments varying in size.

The partition members may be removable or fixed in place. In accordance with one embodiment, the partition is movable. Such movable partitions permit, for example, for cultivating organisms in one compartment and transferring them to another compartment for harvesting and/or sedimentation. It is noted that in order to transfer organisms from one compartment to the other, it is not require to completely remove the partition member from the tank, and in fact, at times, it would suffice only to slightly lift the partition member to allow the cultured organism to flow from a bottom end (bottom level) of one compartment to a bottom end (bottom level) of a following compartment.

When fixed in place, the partition members may be equipped with valve, such as a solenoid-controlled valve, to be typically located at or near the bottom of the partition member, which can open or close as needed. When the valve is open, all the compartments within a tank are inter-connected. The valve can be closed, for example, when an accident occurs, (e.g., container leaking, sidewalls broken), or as otherwise desired by the operator. One benefit of a multicompartent tank is that in case one particular compartment is damaged, the rest of the tank compartments will still hold part of the culture suspension. In addition or alternatively, one compartment may be utilized as a settling compartment where the organism, such as algae is settled at the bottom or top of that compartment before harvesting. Organism may settle at the bottom of the tank or at times, if desired, float at the top area of the medium within the tank, e.g. during culturing and before the need to harvest. In addition or alternatively, the use of a partition member may allow cultivating organisms in one compartment and leaving the other free of organism (e.g. as a backup tank) or even cultivating different organisms in different compartments.

When using a multi-compartment tank, the system can include for each compartment a dedicated aeration arrangement (gas emitting element) as well as a dedicated outlet port. Alternatively, a single outlet port may be utilized and located at the bottom of a single compartment, e.g. designated as the settling compartment and liquid matter is communicated between one compartment to its successive compartment by an overflow principle or via a slot at the bottom end of the partition member.

In one embodiment, fluid communication between one compartment to an adjacent compartment may be provided by means of gravity-caused fluid flow over their common (partition) wall. In some other embodiments, communication between compartments may be by using a pump.

The partition member can be made of any material suitable for inclusion in a system for supporting aquatic organism growth, including but not limited to glass, fiberglass, stainless steel plate, polycarbonate plastic sheet (produced by vacuum molding), and plastic sheet.

The system may also comprise a tank, removable, top cover to prevent airborne-dusts/microbial organisms from entering the culture, and to prevent or at least minimize water evaporation, heat loss, and gas transfer. The cover can be made of a rigid material, such as glass or plastic materials or from elastic one, and is preferably transparent or semi transparent (e.g. at least 75% light transmittance) to allow light to penetrate into the medium from the top surface of the tank. In some embodiments, the top is made of the same material of the sidewalls. In some embodiments, the cover is made of a material that blocks some or all of the transition of ultraviolet or infrared light, while allowing transition of visible light to support photosynthesis.

Figure 8B:
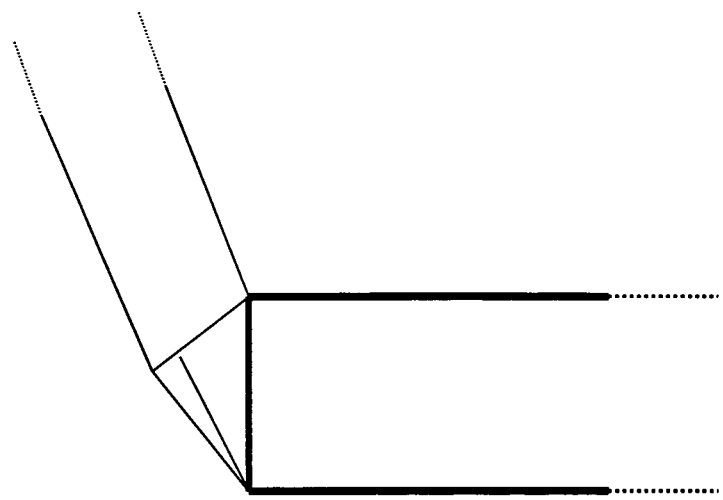
FIGS. 8A and 8B provide two examples of a tank top cover to be employed in accordance with some embodiments of the invention.
Figure 8A:
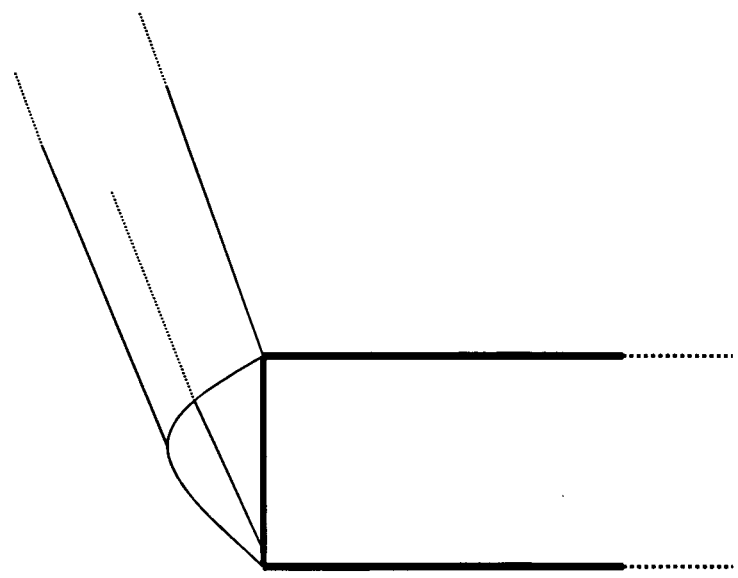

In some embodiments, the cover has a curvature (hemispherical shape FIG. 8A) or an angle directed upwards (FIG. 8B). A cover with a curved shape (FIG. 8A) or angle (FIG. 8B) will prevent accumulation of water drops with or without algal cells on the inner surface of the cover. Potential build up of water drops and/or growing algal cells on the inner surface of the cover will reduce light penetration into the culture. The cover is designed in a manner that will allow its easy removal and reset on the tank or load bearing structure, e.g. for cleaning of system, and convenient access to the tank, as needed.

In a further embodiment, the system may comprise a temperature control element comprising a heating/cooling apparatus and a temperature sensor (not illustrated). Any suitable heating/cooling apparatus can be used. For example, one or more cooled water pipes can be placed at or near the bottom of a sun-facing sidewall of the tank. The temperature of the culture medium within the tank depends on the type of aquatic organism cultivated therein. Typically, for cultivating algae, the temperature control element preferably maintains the temperature of the medium at a temperature ranging from about 15° C. to about 37° C., and preferably from about 20° to about 30° C.

At times, in order to maintain an essentially constant temperature of the fluid within the tank, the tank may be submerged in a liquid reservoir, as further described below.

Further, the system may be equipped with liquid level indicators (not illustrated) to maintain a generally constant volume of culture medium in the culture tank. Level indicators may include, without being limited thereto, float valves, electronic water level detectors etc.

The system may further comprise elements and sensors (not illustrated) for controlling the cultures' temperature, pH, the $NO_3^-/PO_4^{3-}$ levels, and $O_2$ and $CO_2$ concentrations, nutrient concentration, an algae density population.

Further, optical-density sensors, potentiometric sensors, etc., can be inserted into the tank for on-line monitoring of density, e.g. algal cell density, which in turn will be used to control the timing of algal harvesting.

Any monitoring and control elements and sensors can be implemented using an automatic control system and methodology. In some embodiments, a computer-based control and monitoring module is integrated into the system, to monitor and regulate culture's pH, temperature, $NO_3^-/PO_4^{3-}$ levels, $O_2$ and $CO_2$ concentrations, culture medium level etc. and upon need actuate a change in one or more of these conditions.

The various monitoring and control elements may be in wired or wireless communication with the computer based control module, where the control module receives data from the monitoring elements (via one or more dedicated transmitters) and use it to appropriately control the operation of the cultivating system.

The cultivating system of the invention may be constructed for use above ground; and, it is also an option that at least part of the tank is submerged in a water reservoir, such as a pond, lake, sea etc. Maintaining the tank in a water reservoir may help regulating the temperature of the culture medium in the cultivation tank and minimize the effect of external temperature on the conditions within the tank.

Also provided herein is a cultivating plant for cultivating aquatic organisms that comprise an assembly of two or more cultivating systems according to the invention. In accordance with this aspect of the invention, the plurality of cultivating systems may form an arrangement of systems to concomitantly and at times synchronically cultivate the same or different aquatic organism.

In the plant, the plurality of cultivating systems may have the same or different sizes and shapes, and in accordance with one embodiment, are in fluid communication. The plurality of systems may be configured in series and/or in parallel.

In one embodiment, the individual cultivating systems may each be in direct fluid communication at the inlet, i.e. the inlet supplying culture medium, etc. to each of the systems in the arrangement; they may be in direct fluid communication, such that one or more systems receive fluid from one or more upstream systems and one or more feed one or more downstream systems until reaching a final system from which the organism is harvested. The harvesting may be from a final system and/or from a plurality of systems through outlet ports connected to a common harvesting/draining manifold system.

When using an assembly of cultivating systems, each system may be individually equipped with monitoring and control elements such as those described above and also individually be connected (via wire or wireless) to a computer based control and monitoring module also as described above.

In operation, aquatic microorganism, and in this particular exemplary embodiment, algae are mixed with a suitable algal growth medium to form a liquid algal suspension. Those versed in the art will know how to select the appropriate growth medium for a specific algae or mixture of algae. For example, for green algae, the growth medium may be any saline water, such as, seawater, brackish water, etc. The algal suspension is then introduced into the cultivating tank of the invention. The culturing tank is submerged partially in a water reservoir and gas emitting arrangement is activated to introduce, in a controlled manner air, $CO_2$ as well as other gaseous nutrients into the medium.

The algal suspension is exposed to light, sunlight and/or artificial light. Depending on the amount of light, the cell density, the level of pH etc, sensed by the dedicated sensors, the control and monitoring module manipulates the angles of the slanted sidewalls using the adjustable struts so as to allow controlled exposure of the surface area of the culture medium to light and thereby controlled growth of the algae in the medium.

During cultivation, control module allows monitoring of the algal density, and other parameters required for control growth of the algae, as described above. Upon need, the culture medium may be filled or drained according to indications received by the control module, to maintain the required density of the algal population. Once the population of the algae in the tank reaches a desired level, outlet port may open, to allow collection of the algal population in a collection container and isolating the algae by centrifugation, membrane filtration or any other chosen method.

The operation of the system for growing aquatic organism may be as a continuous process, a batch process as well as a combination of continuous and batch process.

When operated as a batch process, algae are introduced into the tank and after a predetermined time or at a predetermined algae concentration, all algae are removed from the tank via a dedicated outlet and new algae suspension is introduced for a following growing cycle.

When operated as a continuous-batch process, the cultivated alga is fully harvested and a small but substantial portion of the same strain of algae, grown in a controlled environment, is used as a "starter" for a new cultivation cycle.

At times, the system may be operated such that fresh water is continuously introduced into one compartment of the tank, typically a first compartment in a series of successive compartments, while cultivated algae are collected from the compartment or from another compartment, typically the last in the series of compartments, at a time point where the desired algal concentration is reached.

When cultivating algae, the algae may have various applications. For instance, the algae may be used for lipid production, fish meal, antioxidants, cartenoides, proteins, food additives, vitamins, polysaccharides, as known to those versed in the art of algae cultivation.

While the invention has been described using the above illustrative examples, many modifications and variations are possible. It is therefore to be understood that the invention is not intended to be limited in any way, other than by the scope of the appended claims.

Description of Non-Limiting Specific Embodiments

Example 1

Construction of Cultivating Units

Two exemplary systems were designed and constructed: for 500 L and a 1,500 L tank volumes, with different depths and angels as shown in FIGS. 7A and 7B.

The two systems included a load bearing structure made of galvanized iron bars, and a carrier in the form of a metal net having (before angulating) a rectangle shape of the size 2 m×3 m, the gaps of the net having the size of 5 cm×10 cm. The net was angulated and welded onto the metal structure.

The tank was made from a sheet of commercially available transparent PVC (1.37 width), 1 mm width which was welded on its borders to create the inner shape (V) and the required sealing to avoid leaking. The edges of the PVC sheet were punctured to form a series of ringed holes for connecting with the top rims of the load bearing structure. The bottom portion of the PVC contained an outlet for harvesting the biomass, after separation process, the outlet was sealed with a removable tap.

Water irrigation 16 mm polyethylene pipes (Netafim, Israel) were used to bubble air and $CO_2$ to the system. The pipes where placed along the bottom portion of the V shape structure, as illustrated in FIGS. 1 and 2. The pipes were connected to air & $CO_2$ sources, and on the other, anchored to the bottom of the pond. The pipes included openings every 10 cm and 2 mm nozzles were inserted into these openings.

The tank was covered with a cover made from either a transparent plastic polyethylene sheet (smaller tank, dimensions illustrated in FIG. 7A, cover shown in FIG. 7C) or from coated high density polyethylene (Solarig 140 g/m²—light transmittance of 94%, Tank's dimensions illustrated in FIG. 7B, cover shown in FIG. 7D). The cover was stretched over the top opening of the tank and connected to top load bearing structure with hinges (that can be lifted and closed). At the bottom, under the tanks, white canvas was laid down for increasing light exposure through reflection.

The 0.5 m³ and 1.5 m³ systems (FIGS. 7A and 7B, respectively) were filled with artificial sea water (ASW) medium to a total of 450 L and 1,500 L accordingly. Air and water temperatures, as well as water evaporation rate were monitored daily and compared during summer (July-August) and winter (December-January). Evaporation losses during summer and winter were 2.6 L/day to 1.8 L/day in the 0.5 m³ system and 2.1 L/day to 1.7 L/day in the 1.5 m³ systems accordingly.

Example 2

Algae Culturing

Strains and Medium

The two exemplary systems were used to inoculate, separately, *Nannochloropsis* sp., *Dunaliela tertiolecta* and *Coccomyxa* sp. purchased from the culture collection in Scotland (CCAP).

Algae cultures were grown in artificial sea water (ASW and f/2 [Guillard R. R. L. and Ryther J. H. 1962. *Studies of marine planktonic diatoms Cyclotella nana and Detonula confervacea*. J. Microbiol. 8, pp. 229-239; Guillard R. R. L. 1975.

*Culture of phytoplankton for feeding marine invertebrates.* pp 26-60. In Smith W. L. and Chanley M. H (Eds.) Culture of Marine Invertebrate Animals. Plenum Press, New York, USA.]) pH 8.2, according to CCAP protocols (culture collection of algae and protozoa, www.ccap.ac.uk), with continuous air bubbling.

*Dunalialla tertiolecta* was grown to a maximum density of $30$-$55 \times 10^6$ cells/ml, *Nannochloropsis* sp. and *Coccomyxa* sp. were grown to a maximum density of $100$-$450 \times 10^6$ cells/ml.

A designated air blower generated a turbulent flow of sufficient rate (10-40 L/h) in order to re-circulate, mix and keep cells in suspension. The gas $CO_2$ 1%-3% v/v (volume of $CO_2$ in air) was supplemented through the polyethylene pipe at the mentioned rate, and the systems were further controlled by pH and light sensors.

The two systems operated continuously for 2 months and then harvested or operated as a batch with harvesting every 2 weeks. The cultures were grown in open-air, losses of fluid due to evaporation were supplemented with fresh water. Chlorination was used to sterilize all components throughout the inoculation and scale up stages.

Figure 9:
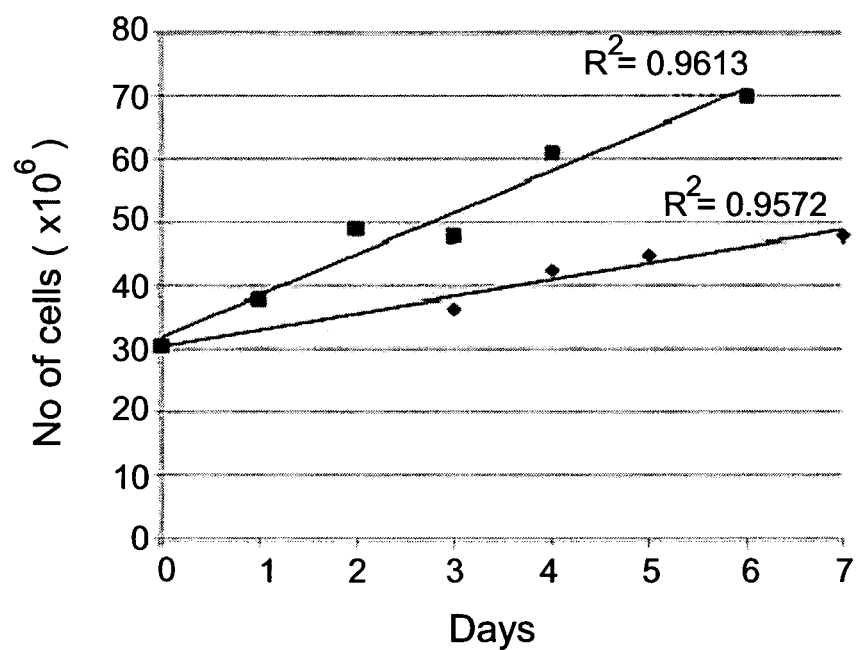
FIG. 9 is a graph showing the effect of turbulence on biomass production (number of cells) in time (days), comparing low turbulence 10-40 L/h (♦) vs. high turbulence 40-100 L/h (■) *Nannochloropsis salina* culture system.

It is noted that when comparing effect of turbulence, by day 7 high turbulence (40-100 L/h) generated more biomass as compared to low turbulence (10-40 L/h) in *Nannochloropsis salina* cultures (FIG. 9).

Scale up Cultivation

Cultivation started indoors in 3 L aeration flasks grown at 20° C. in batch cultures. Flasks were inoculated into 10 L commercially available polyethylene sleeves (100-200 um thick, 5-30 cm wide, 0.5-2 m long) that were further diluted into 20 L outdoor sleeves which were inoculated the two exemplary systems. Cell growth was monitored daily by measuring the absorbance of the culture at 750 nm, microscopy cell counting (Hemacytometer), and chlorophyll extractions. Cells (10 ml of algae culture) were collected by centrifugation (3,000 rpm, 5 minutes) and chlorophyll was extracted using 100% cold acetone until biomass appears colorless. Cell debris was removed by centrifugation and absorbance was measured at 680 nm as known in the art and also described [Richmond A. 2004. *Micro algal Culture*; Biotechnology and Applied Phycology. Blackwell Science publishing, Oxford. UK].

Harvesting and Processing

Samples were taken from the systems to monitor flocculation effect by optical density (OD) reading at 750 nm. Flocculation ended once 95% of the cells sediment, for example an average of 3-4 h for *Nannochloropsis* sp. and *Coccomyxa* sp. and 5-6 h for *Dunaliella tertiolecta*. Settled biomass (10% wet slurry) was collected from an opening at the bottom of the tank using gravitation. Subsequently, each exemplary system was cleaned with 0.001% chlorinated water and was ready for the following cycle of inoculation (batch). Flocculation and harvesting of continuous culture growth was done by pumping out $\frac{1}{8}$-$\frac{1}{10}$ of the volume of each tank to a collecting (600 L) barrel, flocculation and harvesting was done as described above, and slurry was collected from an opening at the bottom of the barrel.

Biomass was dried at 120° C. over night in an oven. Total lipids were extracted using the Soxhelt extractor using n-Hexan as standard solvent [Schafer K. 1998. *Accelerated solvent extraction of lipids for determining the fatty acid composition of biological material.* Anal. Chim. Acta 358 pp. 69-77].

Figure 10A:
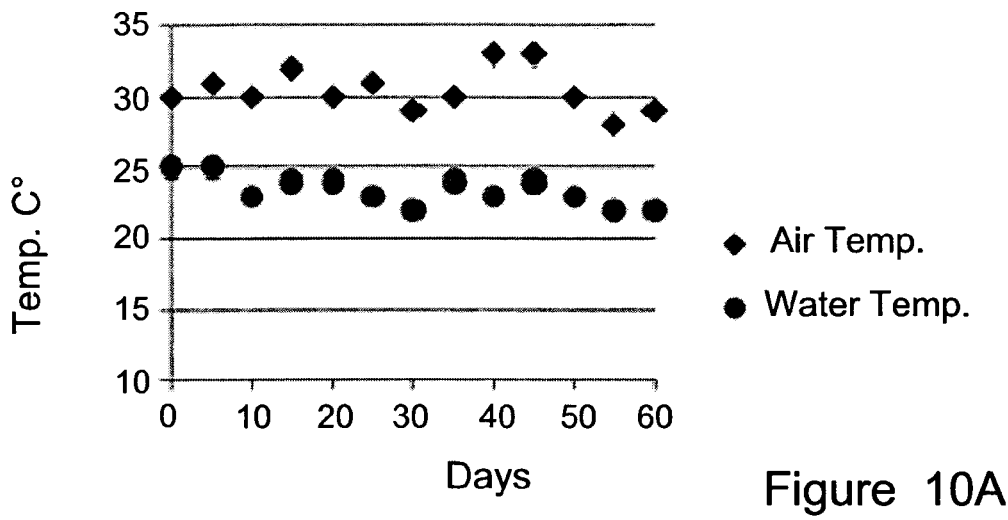
FIGS. 10A-10C are graphs showing conditions of a specific embodiment of the invention when inoculating and cultivating *Coccomyxa* sp in a system in accordance with the invention, FIG. 10A showing the temperature of the air outside the medium and the temperature inside the medium itself during a cultivation cycle.
Figure 10B:
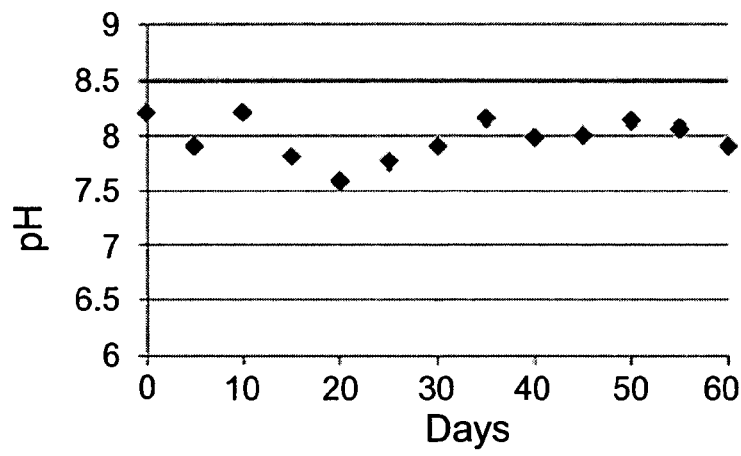
Figure 10C:
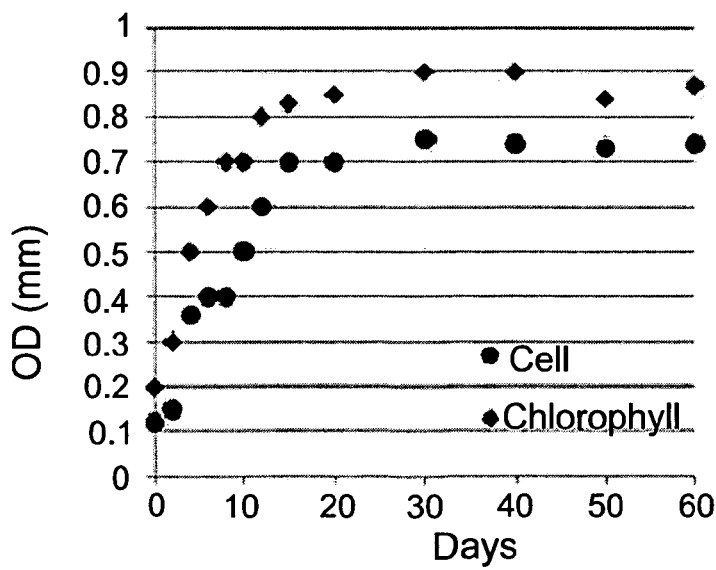

Specifically, *Coccomyxa* sp. was inoculated into the 0.5 $m^3$ system to a final volume of 450 L. Culture pH and controlled supply of $CO_2$ were monitored. FIGS. 10A-10B indicate the control of temperature and pH during a cultivation period of 60 days. The culture reached maximum density by day 12 and remained at steady state for 40 days by diluting the cultures with fresh culture medium (FIG. 10C). Cell density of up to 109 million cells/ml were achieved for *Coccomyxa* sp. and up to 420 and 45 million cells/ml for *Nannochloropsis* sp. and *Dunaliela tertiolecta* accordingly. The vigorous mixing prevented cell concentration at the angulated end of the bottom portion of the tank, with minimal, essentially no adherence to the walls of the tank mid to top level or side walls.

One day before harvesting the culture was flocculated in the tank over night and the cells were concentrated at the bottom of the tank. The biomass was harvested the next day via the opening at the bottom of the tank and dried, as described above.

Maximum dry biomass of *Coccomyxa* sp was 1.55 g/L compared to 2.7 and 2.8 g/L dry biomass of *Nannochloropsis* sp. and *Dunaliela tertiolecta* (Table 1). Productivity of *Coccomyxa* sp was 0.129 g/L/day compared to 0.225 and 0.233 g/L/d of *Nannochloropsis* sp. and *Dunaliela tertiolecta* accordingly.

TABLE 1

Biomass concentration, productivity and specific growth rate of *Nannochloropsis* sp., *Dunaliela tertiolecta* and *Coccomyxa* sp

| Strain | Growth period (Days) | Concentration dry biomass (gr/L) | Productivity (gr/L/day) | Specific growth rate ($\mu$*) |
|---|---|---|---|---|
| *Coccomyxa* sp. | 12 | 1.55 | 0.129 | 0.09 |
| *Nannochloropsis* sp | 12 | 2.7 | 0.225 | 0.18 |
| *Dunaliela tertiolecta* | 12 | 2.8 | 0.233 | 0.14 |

*Specific growth rate ($\mu$) is expressed as $1/n * LN(N1/N2)$ where n = number of growth days, N1 = number of cells per ml on last day and N2 = number of cells per ml on day 1

Example 3

Lipid Production

*Nannochloropsis salina* was grown for 10 days in f/2 medium, PH 8.2, with $KNO_3$ that was used as the only nitrogen source. The pH was maintained in the range of 7-8 and controlled the levels of $CO_2$ supply. Natural lipids accumulated 24 h after reaching maximal cell density (early stationary phase) 2.0-2.8 g/L or in response to nitrogen limitations.

Oil was extracted from dry biomass and triglycerides were analyzed by thin layer chromatography (TLC) using triolein (1 mg/ml) as a standard. Oil content was 25%-35% of dry weight biomass in early stationary phase but under nitrogen limitation, oil accumulated earlier and exceeded 35% (data not shown). Therefore the system of the invention provides an alternative, cost effective, system for growing algae for biofuel or oil, with an advantage of enabling medium variations, in contradiction to some known systems, such as race ways and other open ponds, where the medium cannot be changes during cultivation.

Example 4

Algae Culturing in U-Shape System vs. V-Shape System

Strains and Medium

*Nannochloropsis salina* was grown in the transparent V shape system (1,500 L, 1 m deep) exemplified above, as well as in a sealed (non-transparent) bath having the dimensions of 1.5 m long, 0.5 m wide and 0.5 m deep (250 L) and a U shape at its cross section.

The algae were grown under same conditions as described above, during the summer (July and August). The following are the findings of this comparative study:

Growth rate in the transparent V-shape systems was greater than the growth rate in non-transparent U-shape system. Without being bound by theory, it is believed that the exposure to light via the sidewalls together with the V-shape, which allows better turbulence in the system, increased the total growth rate.

Algae adhered onto the sidewalls of the U-shape system, which made the harvesting by flocculation impossible and necessitated the use of other means form harvesting the algae, such as centrifuging.

The 1,500 L system, having a deeper bottom performed better in maintaining constant temperatures at the bottom end, and lower evaporation rate over time, as compared to the relatively shallow 0.5 m deep V-shape system as well as U shape system.

The immediate conclusion may be that the system of the invention provides for large scale production of algae. It is known that culturing from diluted inoculums may result in photo-inhibition damages and with competition of the cultured organism by bacteria, fungi, protozoa and other algae species. On the other hand, starting with large inoculums volume requires a large nursery, increasing land demand and costs.

The depth and volume of the growth system disclosed herein can be easily adapted to culture densities. In this state smaller volumes will provide higher concentrations. It is important to keep the culture at an exponential growth phase avoiding the sensitive lag phase or the stationary phase to ensure that the desired species dominate the culture and that the culture is at a healthy stage. Furthermore, scale up using the same growth system extended the exponential phase, increasing productivity of the culture. Once the growth system reached its maximal volume, the system can be deflated to the starting volume. The extra volume of the culture can be harvest or collected to inoculate new growth systems or larger growth systems.

The invention claimed is:

1. A cultivating system, comprising:
a modular load-bearing structure having a top portion with at least two rims transverse to each other and defining a top plane, and a bottom portion, the load bearing structure comprising galvanized steel or stainless steel and being in the form of a gridded structure or a perforated plate, and one or more of the at least two rims comprising slidably interconnected concentric rim sections;
a tank adapted for receiving therein a growing medium and for cultivating therein aquatic organisms, said tank comprising two or more sidewalls made of a transparent flexible sheet that comprises a synthetic polymer and allows at least 75% light transmittance therethrough, each sidewall attached to one of the rims of the top plane and extending between one of the at least two rims of the top portion and said bottom portion such that the tank is suspended within the load bearing structure comprising gridded carrier walls for holding the tank, such that in at least one cross-section taken along a plane perpendicular to said top plane, at least two of the sidewalls form a general V-shape converging towards said bottom portion; and
a gas emitting arrangement linkable to a source of pressurized gas and comprising gas emitting nozzles disposed within the tank at said bottom portion.

2. The system according to claim 1, wherein said top portion defines a parallelepiped with two essentially parallel top rims.

3. The system according to claim 2, wherein the length of two or more sides of said parallelepiped can be adjusted.

4. The system according to claim 1, wherein the load-bearing structure comprises legs and at least a top frame carried on said legs, said tank being supported by said top frame.

5. The system according to claim 1, wherein the general V-shape formed by the at least two sidewalls is defined by an angle, the angle being between 60° and 120°.

6. The system according to claim 5, wherein the angle is between 85° and 95°.

7. The system according to claim 1, comprising light reflecting elements configured for reflecting light onto at least the slanted sidewalls.

8. The system according to claim 1, comprising light emitting elements configured for emitting light at least onto the slanted sidewalls.

9. The system according to claim 1, comprising light emitting elements at least partially submerged within the tank.

10. The system according to claim 1, comprising one or more sensors for detecting one or more of the system's temperature, pH, nutrient concentration, gas concentration, organism density, liquid level, and light exposure.

11. The system according to claim 1, comprising at least one inlet port and at least one outlet port for respectively introducing or withdrawing matter from the tank.

12. The system according to claim 1, wherein the tank is at least partially submerged within a body of water.

13. The system according to claim 1, comprising at least one partition wall extending upwards to the tank's top end to divide the tank into two or more compartments and a gas emitting arrangement linkable to a source of pressurized gas; and comprising gas emitting nozzles disposed within at least one of said compartments.

14. The system according to claim 1, comprising at least one anchor for tightly connecting between the tank and said bottom portion.

15. The system according to claim 14, wherein said at least one anchor stretches a bottom portion of the tank towards said load bearing structure to maintain a V-shaped cross section.

16. The system according to claim 1, comprising a carrier for maintaining said tank in a general V-shape configuration.

17. The system according to claim 16, wherein said carrier is in a form of a mesh.

18. A cultivating plant for cultivating aquatic organisms, comprising a plurality of systems according to claim 1.

19. The cultivating plant according to claim 18, wherein said plurality of systems, being the same or different from each other, are connected to a control and monitor module for concomitant cultivation of one or more types of aquatic organisms.

20. The cultivating system of claim 1, wherein said gridded structure is symmetrical or asymmetrical.

21. The cultivating system of claim 1, wherein at least a portion of the two or more sidewalls comprises a coated woven polyethylene sheet.

22. The cultivating system of claim 1, wherein the slidably interconnected concentric rim sections are tubular.

23. A cultivating system, comprising:
a load-bearing structure having a top portion with at least two rims transverse to each other and defining a top plane, and a bottom portion, one or more of the at least two rims comprising slidably interconnected concentric rim sections;

a tank adapted for receiving therein a growing medium and for cultivating therein aquatic organisms, said tank comprising two or more sidewalls made of a transparent flexible sheet that comprises a one or more synthetic polymer materials selected from the group consisting of a high density polyethylene (HDPE) coated with a low density polyethylene (LDPE), a coated polypropylene woven sheet, a polyolefin woven material, polyethylene terephthalate (PET), a low density polyethylene (LDPE), a biaxially orientated polypropylene (BOPP) film, a linear Low density polyethylene (C4 LLDPE), a metallocene catalysed polyolefin plastomer and polyvinylchloride (PVC), each sidewall attached to one of the rims of the top plane and extending between one of the at least two rims of the top portion and said bottom portion such that the tank is suspended within the load bearing structure comprising gridded carrier walls for holding the tank, such that in at least one cross-section taken along a plane perpendicular to said top plane, at least two of the sidewalls form a general V-shape converging towards said bottom portion; and a gas emitting arrangement linkable to a source of pressurized gas and comprising gas emitting nozzles disposed within the tank at said bottom portion.

24. The cultivating system of claim 23, wherein the polyolefin woven material is selected from the group consisting of Vinyl Acetate (EVA), LDPE, polyvinyl alcohol (PVA).

25. The cultivating system of claim 24, wherein the polyolefin woven material is coated with a water impermeable layer.

26. The cultivating system of claim 24, wherein the metallocene catalysed polyolefin plastomer is Hexene or Octene.

27. The cultivating system of claim 23, wherein the slidably interconnected concentric rim sections are tubular.

* * * * *